United States Patent
Paton et al.

(10) Patent No.: US 6,716,432 B1
(45) Date of Patent: Apr. 6, 2004

(54) PNEUMOLYSIN MUTANTS AND PNEUMOCOCCAL VACCINES MADE THEREFROM

(76) Inventors: James Cleland Paton, 49 Foster St., Parkside, S.A. 5063 (AU); David John Hansman, 66 Alexandra Avenue, Rose Park, S.A. 5067 (AU); Graham John Boulnois, The Coach House, Brook Lane, Alderley Edge, Cheshire, SK9 7QJ (GB); Peter William Andrew, 7 Chapel Lane, Leister, Leistershire LE1 9HN (GB); Timothy John Mitchell, 25 Mawbys Lane, Appleby Magna, Burton-on-Trent Straffordshire DE12 7AA (GB); John Arthur Walker, No. 11 Traymore Apts., 51 S. McLean, Memphis, TN (US) 38104

( * ) Notice: Subject to any disclaimer, the term of this patent is extended or adjusted under 35 U.S.C. 154(b) by 0 days.

(21) Appl. No.: 08/378,213

(22) Filed: Jan. 25, 1995

(Under 37 CFR 1.47)

Related U.S. Application Data

(63) Continuation-in-part of application No. 08/290,501, filed on Aug. 15, 1994, now abandoned, which is a continuation-in-part of application No. 07/721,444, filed on Jul. 30, 1991, now abandoned.

(30) Foreign Application Priority Data

Dec. 16, 1988 (AU) .................................................. 1989

(51) Int. Cl.$^7$ ........................ A61K 39/00; A61K 39/38; A61K 39/02; A61K 39/09
(52) U.S. Cl. ................ 424/234.1; 424/184.1; 424/185.1; 424/236.1; 424/244.1; 424/190.1; 424/278.1; 530/300; 530/325; 530/350
(58) Field of Search ................ 530/300, 350, 530/325; 424/184.1, 185.1, 236.1, 244.1, 832, 190.1, 278.1

(56) References Cited

FOREIGN PATENT DOCUMENTS

WO          WO90/06951       *  6/1990  ........... C07K/13/00

OTHER PUBLICATIONS

Attwood. 2000. Science. 290:471–473.*
Boselgo et al. 1991. Vaccines and Immunotheraphy: Gonorrhea Vaccines; Chap. 7. pp. 211–223.*
Ellis. 1988. Vaccines: New Technologies for Making Vaccines. Chap. 29. pp. 568–574.*
Jobling et al. 1991. Mol. Micro. 5(7): 1755–1767.*
Russell et al. 1994. J. Mol. Bio. 244:332–350.*
Mitchell et al.1991. Mol. Micro. 5(5): 1883–1888.*
Johnson et al Abstracts of the Annual Meeting of the American Soc. for Microbiology 1988, page 106, Abst 0–212, Mar. 1, 1997.*
Boulnois et al. ZBL. Bakt. Suppl. 19: 43–51, 1991.*
Walker Dissertation, Apr. 1988, Studies of Pneumolysin, The Membrane Damaging Toxin of *Streptococcus pneumonia*. pp. I, III, 7–8, 12, 89, 90, 106–128, 129–141, Mar. 1, 1997.*

* cited by examiner

Primary Examiner—Lynette R. F. Smith
Assistant Examiner—JaNa A. Hines
(74) Attorney, Agent, or Firm—Young & Thompson

(57) ABSTRACT

Mutants of pneumolysin that are non-toxic by reason of amino acid substitutions have been constructed. These mutants elicit an immune response in animals that is reactive to wild-type pneumolysin. The invention also encompasses vaccines for humans based on these mutants, including vaccines comprising conjugates with pneumococcal capsular polysaccharides.

**21 Claims, 9

Figure 5:
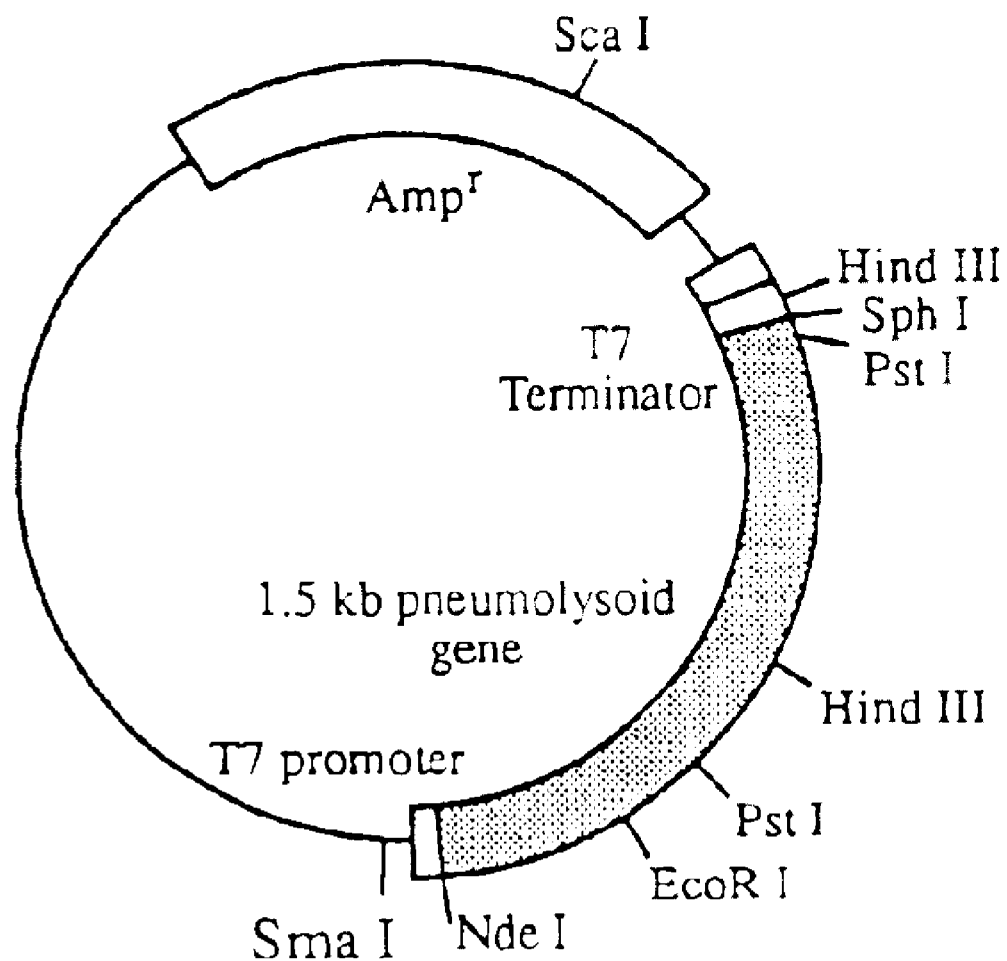

| | | | | |
|---|---|---|---|---|
| AGATGGCAAA | TAAAGCAGTA | AATGACTTTA | TACTAGCTAT | GAATTACGAT |
| AAAAAGAAAC | TCTTGACCCA | TCAGGGAGAA | AGTATTGAAA | ATCGTTTCAT |
| CAAAGAGGGT | AATCAGCTAC | CCGATGAGTT | TGTTGTTATC | GAAAGAAAGA |
| AGCGGAGCTT | GTCGACAAAT | ACAAGTGATA | TTTCTGTAAC | AGCTACCAAC |
| GACAGTCGCC | TCTATCCTGG | AGCACTTCTC | GTAGTGGATG | AGACCTTGTT |
| AGAGAATAAT | CCCACTCTTC | TTGCGGTTGA | TCGTGCTCCG | ATGACTTATA |
| GTATTGATTT | GCCTGGTTTG | GCAAGTAGCG | ATAGCTTTCT | CCAAGTGGAA |
| GACCCCAGCA | ATTCAAGTGT | TCGCGGAGCG | GTAAACGATT | TGTTGGCTAA |
| GTGGCATCAA | GATTATGGTC | AGGTCAATAA | TGTCCCAGCT | AGAATGCAGT |
| ATGAAAAAAT | AACGGCTCAC | AGCATGGAAC | AACTCAAGGT | CAAGTTTGGT |
| TCTGACTTTG | AAAAGACAGG | GAATTCTCTT | GATATTGATT | TTAACTCTGT |
| CCATTCAGGT | GAAAAGCAGA | TTCAGATTGT | TAATTTTAAG | CAGATTTATT |
| ATACAGTCAG | CGTAGACGCT | GTTAAAAATC | CAGGAGATGT | GTTTCAAGAT |
| ACTGTAACGG | TAGAGGATTT | AAAACAGAGA | GGAATTTCTG | CAGAGCGTCC |
| TTTGGTCTAT | ATTTCGAGTG | TTGCTTATGG | GCGCCAAGTC | TATCTCAAGT |
| TGGAAACCAC | GAGTAAGAGT | GATGAAGTAG | AGGCTGCTTT | TGAAGCTTTG |
| ATAAAAGGAG | TCAAGGTAGC | TCCTCAGACA | GAGTGGAAGC | AGATTTTGGA |
| CAATACAGAA | GTGAAGGCGG | TTATTTTAGG | GGGCGACCCA | AGTTCGGGTG |
| CCCGAGTTGT | AACAGGCAAG | GTGGATATGG | TAGAGGACTT | GATTCAAGAA |
| GGCAGTCGCT | TTACAGCAGA | TCATCCAGGC | TTGCCGATTT | CCTATACAAC |
| TTCTTTTTTA | CGTGACAATG | TAGTTGCGAC | CTTTCAAAAC | AGTACAGACT |
| ATGTTGAGAC | TAAGGTTACA | GCTTACAGAA | ACGGAGATTT | ACTGCTGGAT |
| CATAGTGGTG | CCTATGTTGC | CCAATATTAT | ATTACTTGGG | ATGAATTATC |
| CTATGATCAT | CAAGGTAAGG | AAGTCTTGAC | TCCTAAGGCT | TGGGACAGAA |
| ATGGGCAGGA | TTTGACGGCT | CACTTTACCA | CTAGTATTCC | TTTAAAAGGG |
| AATGTTCGTA | ATCTCTCTGT | CAAAATTAGA | GAGTGTACCG | GGCTTGCCTG |
| GGAATGGTGG | CGTACGGTTT | ATGAAAAAAC | CGATTTGCCA | CTAGTGCGTA |
| AGCGGACGAT | TTCTATTTGG | GGAACAACTC | TCTATCCTCA | GGTAGAGGAT |
| AAGGTAGAAA | ATGAC | | | |

FIG. 1  DNA sequence of pneumolysin gene. ATG start codon underlined

| CCATGGCAAA | TAAAGCAGTA | AATGACTTTA | TACTAGCTAT | GAATTACGAT |
|---|---|---|---|---|
| AAAAAGAAAC | TCTTGACCCA | TCAGGGAGAA | AGTATTGAAA | ATCGTTTCAT |
| CAAAGAGGGT | AATCAGCTAC | CCGATGAGTT | TGTTGTTATC | GAAAGAAAGA |
| AGCGGAGCTT | GTCGACAAAT | ACAAGTGATA | TTTCTGTAAC | AGCTACCAAC |
| GACAGTCGCC | TCTATCCTGG | AGCACTTCTC | GTAGTGGATG | AGACCTTGTT |
| AGAGAATAAT | CCCACTCTTC | TTGCGGTTGA | TCGTGCTCCG | ATGACTTATA |
| GTATTGATTT | GCCTGGTTTG | GCAAGTAGCG | ATAGCTTTCT | CCAAGTGGAA |
| GACCCCAGCA | ATTCAAGTGT | TCGCGGAGCG | GTAAACGATT | TGTTGGCTAA |
| GTGGCATCAA | GATTATGGTC | AGGTCAATAA | TGTCCCAGCT | AGAATGCAGT |
| ATGAAAAAAT | AACGGCTCAC | AGCATGGAAC | AACTCAAGGT | CAAGTTTGGT |
| TCTGACTTTG | AAAAGACAGG | GAATTCTCTT | GATATTGATT | TTAACTCTGT |
| CCATTCAGGT | GAAAAGCAGA | TTCAGATTGT | TAATTTTAAG | CAGATTTATT |
| ATACAGTCAG | CGTAGACGCT | GTTAAAAATC | CAGGAGATGT | GTTTCAAGAT |
| ACTGTAACGG | TAGAGGATTT | AAAACAGAGA | GGAATTTCTG | CAGAGCGTCC |
| TTTGGTCTAT | ATTTCGAGTG | TTGCTTATGG | GCGCCAAGTC | TATCTCAAGT |
| TGGAAACCAC | GAGTAAGAGT | GATGAAGTAG | AGGCTGCTTT | TGAAGCTTTG |
| ATAAAAGGAG | TCAAGGTAGC | TCCTCAGACA | GAGTGGAAGC | AGATTTTGGA |
| CAATACAGAA | GTGAAGGCGG | TTATTTTAGG | GGGCGACCCA | AGTTCGGGTG |
| CCCGAGTTGT | AACAGGCAAG | GTGGATATGG | TAGAGGACTT | GATTCAAGAA |
| GGCAGTCGCT | TTACAGCAGA | TCATCCAGGC | TTGCCGATTT | CCTATACAAC |
| TTCTTTTTTA | CGTGACAATG | TAGTTGCGAC | CTTTCAAAAC | AGTACAGACT |
| ATGTTGAGAC | TAAGGTTACA | GCTTACAGAA | ACGGAGATTT | ACTGCTGGAT |
| CATAGTGGTG | CCTATGTTGC | CCAATATTAT | ATTACTTGGG | ATGAATTATC |
| CTATGATCAT | CAAGGTAAGG | AAGTCTTGAC | TCCTAAGGCT | TGGGACAGAA |
| ATGGGCAGGA | TTTGACGGCT | CACTTTACCA | CTAGTATTCC | TTTAAAAGGG |
| AATGTTCGTA | ATCTCTCTGT | CAAAATTAGA | GAGTGTACCG | GGCTTGCCTG |
| GGAATGGTGG | CGTACGGTTT | ATGAAAAAAC | CGATTTGCCA | CTAGTGCGTA |
| AGCGGACGAT | TTCTATTTGG | GGAACAACTC | TCTATCCTCA | GGTAGAGGAT |
| AAGGTAGAA | ATGAC | | | |

FIG. 2  DNA sequence of modified pneumolysin gene. An Ncol restriction site (underlined) has been introduced at the start codon

| | | | | | | | | | | | |
|---|---|---|---|---|---|---|---|---|---|---|---|
| Met 1 | Ala | Asn | Lys | Ala | Val | Asn | Asp | Phe | Ile | Leu 11 | Ala | Met |
| Asn | Tyr | Asp | Lys | Lys | Lys | Leu | Leu 21 | Thr | His | Gln | Gly | Glu |
| Ser | Ile | Glu | Asn | Arg 31 | Phe | Ile | Lys | Glu | Gly | Asn | Gln | Leu |
| Pro | Asp 41 | Glu | Phe | Val | Val | Ile | Glu | Arg | Lys | Lys | Arg 51 | Ser |
| Leu | Ser | Thr | Asn | Thr | Ser | Asp | Ile | Ser 61 | Val | Thr | Ala | Thr |
| Asn | Asp | Ser | Arg | Leu | Tyr 71 | Pro | Gly | Ala | Leu | Leu | Val | Val |
| Asp | Glu | Thr 81 | Leu | Leu | Glu | Asn | Asn | Pro | Thr | Leu | Leu | Ala 91 |
| Val | Asp | Arg | Ala | Pro | Met | Thr | Tyr | Ser | Ile 101 | Asp | Leu | Pro |
| Gly | Leu | Ala | Ser | Ser | Asp | Ser 111 | Phe | Leu | Gln | Val | Glu | Asp |
| Pro | Ser | Asn | Ser 121 | Ser | Val | Arg | Gly | Ala | Val | Asn | Asp | Leu |
| Leu 131 | Ala | Lys | Trp | His | Gln | Asp | Tyr | Gly | Gln | Val 141 | Asn | Asn |
| Val | Pro | Ala | Arg | Met | Gln | Tyr | Glu 151 | Lys | Ile | Thr | Ala | His |
| Ser | Met | Glu | Gln | Leu 161 | Lys | Val | Lys | Phe | Gly | Ser | Asp | Phe |
| Glu | Lys 171 | Thr | Gly | Asn | Ser | Leu | Asp | Ile | Asp | Phe | Asn 181 | Ser |
| Val | His | Ser | Gly | Glu | Lys | Gln | Ile | Gln 191 | Ile | Val | Asn | Phe |
| Lys | Gln | Ile | Tyr | Tyr | Thr 201 | Val | Ser | Val | Asp | Ala | Val | Lys |
| Asn | Pro | Gly 211 | Asp | Val | Phe | Gln | Asp | Thr | Val | Thr | Val | Glu 221 |
| Asp | Leu | Lys | Gln | Arg | Gly | Ile | Ser | Ala | Glu | Arg 231 | Pro | Leu |
| Val | Tyr | Ile | Ser | Ser | Val | Ala 241 | Tyr | Gly | Arg | Gln | Val | Tyr |

FIG. 3A

| | | | | | | | | | | | |
|---|---|---|---|---|---|---|---|---|---|---|---|
| Leu | Lys | Leu | Glu<br>251 | Thr | Thr | Ser | Lys | Ser | Asp | Glu | Val | Glu |
| Ala<br>261 | Ala | Phe | Glu | Ala | Leu | Ile | Lys | Gly | Val | Lys<br>271 | Val | Ala |
| Pro | Gln | Thr | Glu | Trp | Lys | Gln | Ile<br>281 | Leu | Asp | Asn | Thr | Glu |
| Val | Lys | Ala | Val | Ile<br>291 | Leu | Gly | Gly | Asp | Pro | Ser | Ser | Gly |
| Ala | Arg<br>301 | Val | Val | Thr | Gly | Lys | Val | Asp | Met | Val | Glu<br>311 | Asp |
| Leu | Ile | Gln | Glu | Gly | Ser | Arg | Phe | Thr<br>321 | Ala | Asp | His | Pro |
| Gly | Leu | Pro | Ile | Ser | Tyr<br>331 | Thr | Thr | Ser | Phe | Leu | Arg | Asp |
| Asn | Val | Val<br>341 | Ala | Thr | Phe | Gln | Asn | Ser | Thr | Asp | Tyr | Val<br>351 |
| Glu | Thr | Lys | Val | Thr | Ala | Tyr | Arg | Asn | Gly<br>361 | Asp | Leu | Leu |
| Leu | Asp | His | Ser | Gly | Ala | Tyr<br>371 | Val | Ala | Gln | Tyr | Tyr | Ile |
| Thr | Trp | Asp | Glu<br>381 | Leu | Ser | Tyr | Asp | His | Gln | Gly | Lys | Glu |
| Val<br>391 | Leu | Thr | Pro | Lys | Ala | Trp | Asp | Arg | Asn | Gly<br>401 | Gln | Asp |
| Leu | Thr | Ala | His | Phe | Thr | Thr | Ser<br>411 | Ile | Pro | Leu | Lys | Gly |
| Asn | Val | Arg | Asp | Leu<br>421 | Ser | Val | Lys | Ile | Arg | Glu | Cys | Thr |
| Gly | Leu<br>431 | Ala | Trp | Glu | Trp | Trp | Arg | Thr | Val | Tyr | Glu<br>441 | Lys |
| Thr | Asp | Leu | Pro | Leu | Val | Arg | Lys | Arg<br>451 | Thr | Ile | Ser | Ile |
| Trp | Gly | Thr | Thr | Leu | Tyr<br>461 | Pro | Gln | Val | Glu | Asp | Lys | Val |
| Glu | Asn | Asp<br>471 | | | | | | | | | | |

FIG. 3B

| | | | | | | | | | | | |
|---|---|---|---|---|---|---|---|---|---|---|---|
| Met 1 | Ala | Asn | Lys | Ala | Val | Asn | Asp | Phe | Ile | Leu 11 | Ala | Met |
| Asn | Tyr | Asp | Lys | Lys | Lys | Leu | Leu 21 | Thr | His | Gln | Gly | Glu |
| Ser | Ile | Glu | Asn | Arg 31 | Phe | Ile | Lys | Glu | Gly | Asn | Gln | Leu |
| Pro | Asp 41 | Glu | Phe | Val | Val | Ile | Glu | Arg | Lys | Lys | Arg 51 | Ser |
| Leu | Ser | Thr | Asn | Thr | Ser | Asp | Ile | Ser 61 | Val | Thr | Ala | Thr |
| Asn | Asp | Ser | Arg | Leu | Tyr 71 | Pro | Gly | Ala | Leu | Leu | Val | Val |
| Asp | Glu | Thr 81 | Leu | Leu | Glu | Asn | Asn | Pro | Thr | Leu | Leu | Ala 91 |
| Val | Asp | Arg | Ala | Pro | Met | Thr | Tyr | Ser | Ile 101 | Asp | Leu | Pro |
| Gly | Leu | Ala | Ser | Ser | Asp | Ser 111 | Phe | Leu | Gln | Val | Glu | Asp |
| Pro | Ser | Asn | Ser 121 | Ser | Val | Arg | Gly | Ala | Val | Asn | Asp | Leu |
| Leu 131 | Ala | Lys | Trp | His | Gln | Asp | Tyr | Gly | Gln | Val 141 | Asn | Asn |
| Val | Pro | Ala | Arg | Met | Gln | Tyr | Glu 151 | Lys | Ile | Thr | Ala | His |
| Ser | Met | Glu | Gln | Leu 161 | Lys | Val | Lys | Phe | Gly | Ser | Asp | Phe |
| Glu | Lys 171 | Thr | Gly | Asn | Ser | Leu | Asp | Ile | Asp | Phe | Asn 181 | Ser |
| Val | His | Ser | Gly | Glu | Lys | Gln | Ile | Gln 191 | Ile | Val | Asn | Phe |
| Lys | Gln | Ile | Tyr | Tyr | Thr 201 | Val | Ser | Val | Asp | Ala | Val | Lys |
| Asn | Pro | Gly 211 | Asp | Val | Phe | Gln | Asp | Thr | Val | Thr | Val | Glu 221 |
| Asp | Leu | Lys | Gln | Arg | Gly | Ile | Ser | Ala | Glu | Arg 231 | Pro | Leu |
| Val | Tyr | Ile | Ser | Ser | Val | Ala 241 | Tyr | Gly | Arg | Gln | Val | Tyr |
| Leu | Lys | Leu | Glu 251 | Thr | Thr | Ser | Lys | Ser | Asp | Glu | Val | Glu |

FIG. 4A

```
                Trp
                 |
Ala  Ala   Phe  Glu  Ala  Leu  Ile  Lys  Gly  Val  Lys  Val  Ala
261                                                271
                      Phe
                       |
Pro  Gln  Thr   Glu  Trp  Lys  Gln  Ile  Leu  Asp  Asn  Thr  Glu
                                    281

Val  Lys  Ala   Val  Ile  Leu  Gly  Gly  Asp  Pro  Ser  Ser  Gly
                      291

Ala  Arg  Val   Val  Thr  Gly  Lys  Val  Asp  Met  Val  Glu  Asp
301                                                     311

Leu  Ile  Gln   Glu  Gly  Ser  Arg  Phe  Thr  Ala  Asp  His  Pro
                                         321

Gly  Leu  Pro   Ile  Ser  Tyr  Thr  Thr  Ser  Phe  Leu  Arg  Asp
                           331

Asn  Val  Val   Ala  Thr  Phe  Gln  Asn  Ser  Thr  Asp  Tyr  Val
           341                                               351

Glu  Thr  Lys   Val  Thr  Ala  Tyr  Arg  Asn  Gly  Asp  Leu  Leu
                                              361
           Arg
            |
Leu  Asp  His   Ser  Gly  Ala  Tyr  Val  Ala  Gln  Tyr  Tyr  Ile
                                    371
      Phe                           Phe  Asn
       |                             |    |
Thr  Trp  Asp   Glu  Leu  Ser  Trp  Asp  His  Gln  Gly  Lys  Glu
                 381

Val  Leu  Thr   Pro  Lys  Ala  Trp  Asp  Arg  Asn  Gly  Gln  Asp
391                                                 401

Leu  Thr  Ala   His  Phe  Thr  Thr  Ser  Ile  Pro  Leu  Lys  Gly
                                    411
                                                        Ala
                                                         |
                                                        Gly--Ser
                                                         |
Asn  Val  Arg   Asp  Leu  Ser  Val  Lys  Ile  Arg  Glu  Cys  Thr
                      421
                      Ala
                       |
                Phe   Gln  Phe  Phe
                 |     |    |    |
Gly  Leu  Ala   Trp  Glu  Trp  Trp  Arg  Thr  Val  Tyr  Glu  Lys
           431                                               441

Thr  Asp  Leu   Pro  Leu  Val  Arg  Lys  Arg  Thr  Ile  Ser  Ile
                                              451

Trp  Gly  Thr   Thr  Leu  Tyr  Pro  Gln  Val  Glu  Asp  Lys  Val
                           461

Glu  Asn  Asp
           471
```

FIG. 4B

PNEUMOLYSIN MUTANTS AND PNEUMOCOCCAL VACCINES MADE THEREFROM

This application is a continuation-in-part of application Ser. No. 08/290,501, filed Aug. 15, 1994, now abandoned, which a continuation-in-part of Ser. No. 07/721,444, filed Jul. 30, 1991, now abandoned, which was the 35 USC §371 national phase of International application PCT/AU89/00539, filed on Dec. 15, 1989, which designated the United States of America.

This invention relates to mutants of the toxin pneumolysin and pneumococcal vaccines based on these mutants.

BACKGROUND OF THE INVENTION

*Streptococcus pneumoniae* (pneumococcus) is an important pathogen, causing invasive diseases such as pneumonia, meningitis and bacteremia. Even in regions where effective antibiotic therapy is freely available, the mortality rate from pneumococcal pneumonia can be as high as 19% in hospitalized patients and this increases to 30–40% in patients with bacteremia. These high mortality rates have been reported in the U.S.A. where pneumonia, of which *S. pneumoniae* is the commonest cause, is the fifth ranking cause of death. Indeed, pneumonia is the only infectious disease among the top ten causes of death in that country. In the United States mortality rates for pneumococcal meningitis range from 13–45%. In developing countries, in excess of 3 million children under the age of 5 years die each year from pneumonia, and again *S. pneumoniae* is the commonest causative agent. *S. pneumoniae* also causes less serious, but highly prevalent infections such as otitis media and sinusitis, which have a significant impact on health-care costs in developed countries. Otitis media is especially important in young children; sinusitis affects both children and adults.

In the late 1970's, a vaccine was licensed for the purpose of preventing serious infections, especially bacterial pneumonia and for protecting certain groups, such as splenectomized individuals and young children, who are particularly susceptible to fulminating pneumococcal disease. The vaccine is composed of purified capsular polysaccharides, which are the predominant pneumococcal surface antigens. However, each serotype of *S. pneumoniae* (of which there are 83) has a structurally distinct capsular polysaccharides, and immunization with one serotype confers no protection whatsoever against the vast majority of the others. The vaccine currently licensed in Australia contains polysaccharides purified from the 23 most common serotypes, which account for approximately 90% of pneumococcal infections in this country.

Protection even against those serotypes contained in the vaccine is by no means complete, and there have been several reports of serious, even fatal infections occurring in vaccinated high-risk individuals. The efficacy of the vaccine is poorest in young children, and several studies, including one conducted in Adelaide, have shown that the existing formulation has little or no demonstrable clinical benefit in this group. This apparent failure cm the vaccine appears to be related to the poor immunogenicity of certain pneumococcal polysaccharides in children under 5 years of age. We have shown that the antibody response is particularly poor to the five serotypes which most commonly cause disease in children (types 6, 14, 18, 19 and 23). Indeed, the antibody response to these pneumococcal polysaccharides only approaches adult levels in children over 8 years of age at the time of vaccination.

In view of this, a vaccine, including antigens other than the capsular polysaccharides seems to be required to protect young children from pneumococcal infection. One such antigen could be pneumolysin, a protein toxin produced by all virulent *S. pneumoniae* isolates.

Immunization of mice with this protein has been found to confer a degree of protection from pneumococcal infection. However there is a difficulty in that pneumolysin is toxic to humans. Thus pneumolysin included in a vaccine must therefore be substantially non-toxic. However, the rendering of a pneumolysin non-toxic by most currently employed methods would be likely to alter the basic configuration of the protein so as to be immunogenically distinct from the native or wild-type pneumolysin. An immune response elicited by an altered protein that is immunogenically distinct from the native pneumolysin will have a decreased protective capacity or no protective capacity. Thus the difficulty is to produce an altered pneumolysin that is non-toxic and at the same time sufficiently immunogenically similar to the toxic form to elicit a protective immune response.

An altered pneumolysin with the above characteristics can then be used in a number of ways in a vaccine. Thus the altered pneumolysin may be used by itself to immunize, or alternatively the altered pneumolysin may be conjugated to pneumococcal polysaccharide, or alternatively may be included in a vaccine wherein pneumococcal polysaccharides may be conjugated to another protein and the altered pneumolysin is present in a non-conjugated form only. Alternatively, pneumococcal polysaccharide and pneumolysin may both be used in an unconjugated form.

DESCRIPTION OF INVENTION

In a broad form therefore the invention may be said to reside in an altered pneumolysin being substantially non-toxic and being capable of eliciting an immune response in an animal susceptible to wild-type pneumolysin.

Preferably the altered pneumolysin has reduced complement binding activity as compared to wild-type pneumolysin. Reduction in the complement binding activity results in less inflammation at the site of administering the vaccine.

Preferably the altered pneumolysin has reduced Fc binding activity as compared to wild-type pneumolysin. Reduction in the Fc binding activity results in less inflammation at the site of administering the vaccine.

Preferably the altered pneumolysin is altered by reason of one or more amino acid substitutions relative to wild-type pneumolysin.

The pneumolysin may be altered in that the amino acid present at any one or more than one of residue sites 367, 384, 385, 428, 433 or 435 of wild-type pneumolysin are replaced, removed or blocked.

In a further form the invention could be said to reside in a vaccine including an altered pneumolysin, said altered pneumolysin being nontoxic and being capable of eliciting an immune response in an animal being reactive to wild-type pneumolysin.

Preferably the vaccine comprises capsular polysaccharide material conjugated with the altered pneumolysin.

The capsular material may be derived from any one or more of the *Streptococcus pneumoniae* serotypes 6A, 6B, 14, 18C, 19A, 19F, 23F, 1, 2, 3, 4, 5, 7F, 8, 9N, 9V, 10A, 11A, 12F, 15B, 17F, 20, 22F and 33F.

In this embodiment, serotypes which are commonly associated with disease in children, and to which children generally have a poor immune response, may be specifically targeted (i.e. Danish serotypes 6A, 6B, 14, 18C, 19A, 19F and 23F). Other common serotypes contained in the present 23-valent Merck Sharp and Dohme vaccine (Pneumovax 23) however, could also be used to synthesize conjugates (i.e. types 1, 2, 3, 4, 5, 7F, 8, 9N, 9V, 10A, 11A, 12F, 15B, 17F, 20, 22F and 33F) or indeed any other serotype. Conjugation of any pneumococcal polysaccharides to the protein carrier ensures good T-cell dependent immunogenicity in children, such that protective levels of anti-polysaccharide antibody are produced.

The combination of the altered pneumolysin together with the capsular material will ensure an extra degree of protection, particularly against serotypes of *S. pneumoniae* whose polysaccharides are not incorporated in the existing vaccine formulations.

The vaccine is preferably administered by sub-cutaneous injection, with or without an approved adjuvant, such as alumina gel.

In another form the invention could be said to reside in a recombinant clone including a replicon and a DNA sequence encoding an altered pneumolysin, said altered pneumolysin being non-toxic and being capable of eliciting an immune response in an animal susceptible to wild-type pneumolysin.

In yet another form the invention could be said to reside in a method of producing an altered pneumolysin including the steps of purifying said altered pneumolysin from an expression system including a recombinant clone with DNA encoding an altered pneumolysin said pneumolysin being substantially non-toxic and being capable of eliciting an immune response in an animal susceptible to wild-type pneumolysin.

Preferably the expression system is a culture of a host cell including a recombinant clone with DNA encoding the altered pneumolysin.

In another form the invention could be said to reside in a method of producing a vaccine including the step of amplifying-a recombinant clone encoding an altered pneumolysin, inducing transcription and translation of said cloned material, the purification of altered pneumolysin, and the step of conjugating the altered pneumolysin with a capsular polysaccharide, the altered pneumolysin having substantially reduced toxic activity as compared with wild-type pneumolysin.

Figure 6:
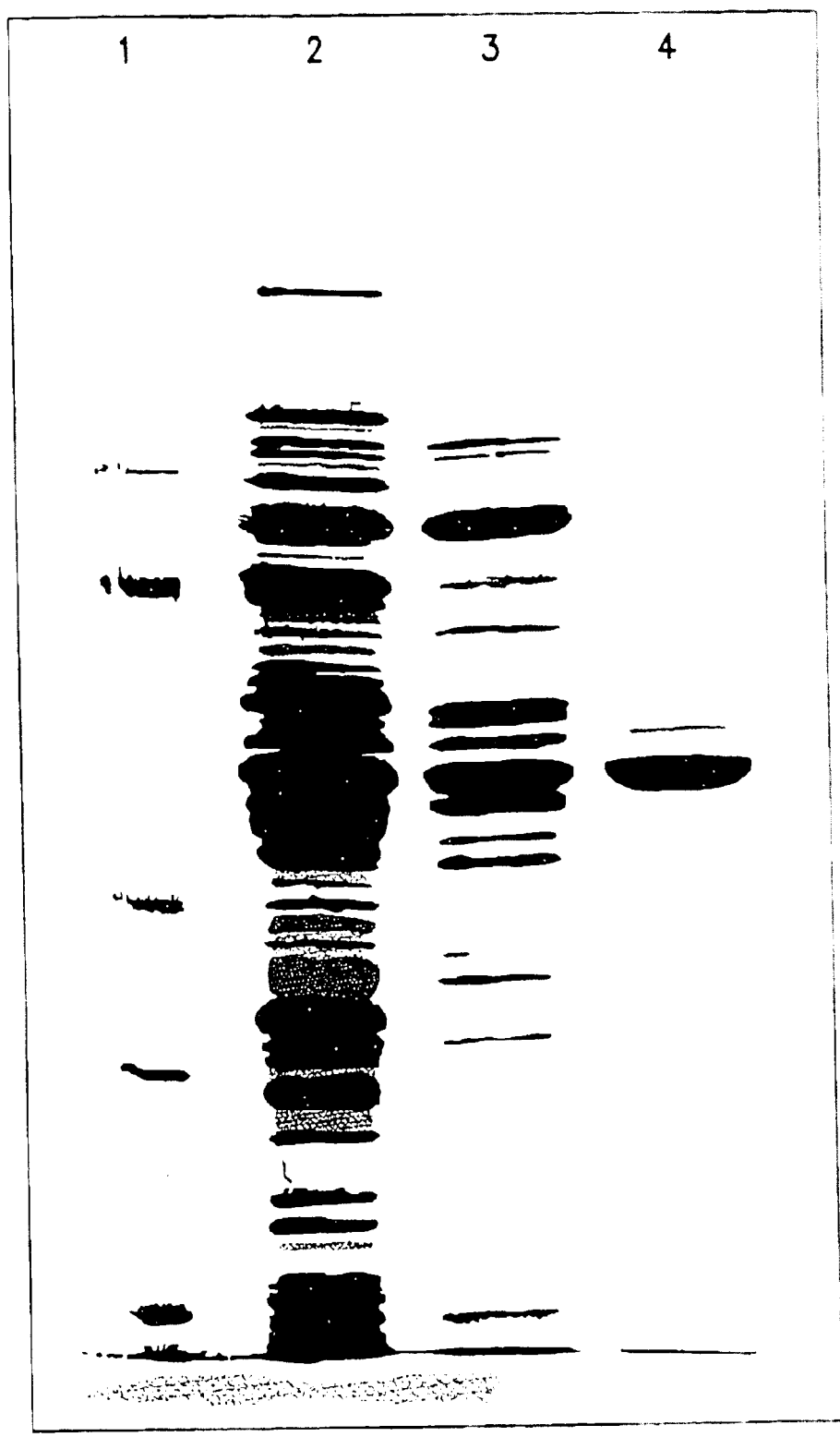
Figure 7:
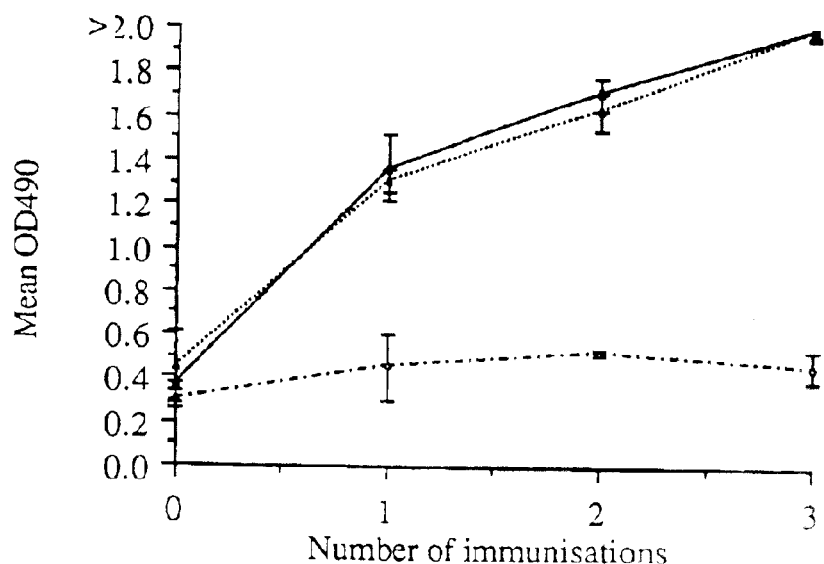
Figure 8:
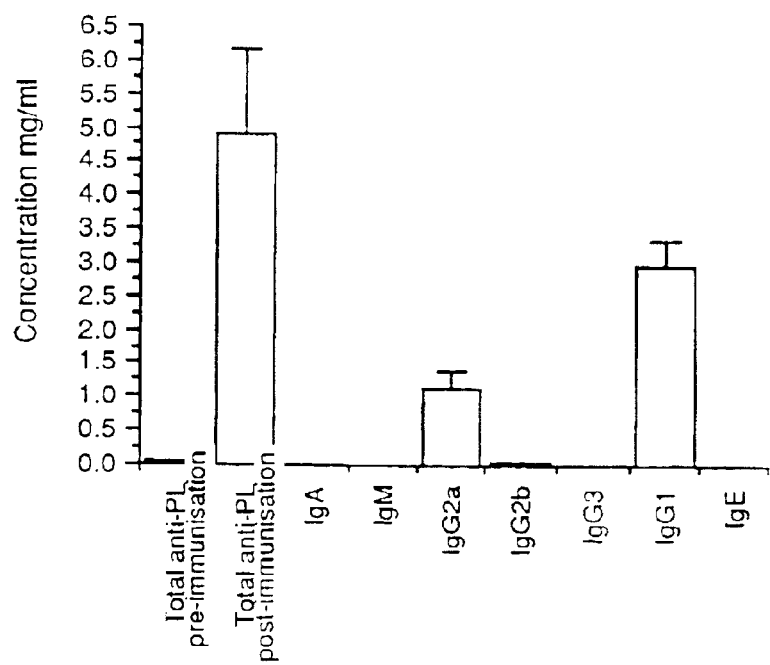

For a better understanding of the invention specific embodiments of the invention will now be described with reference to diagrams wherein:

FIG. 1 is the DNA sequence of the gene encoding wild-type pneumolysin (SEQ ID NO:1);

FIG. 2 is the DNA sequence (SEQ ID NO:3) of an altered gene encoding wild type pneumolysin used for cloning the pneumolysin gene into an expression vector, FIGS. 3a and 3b show the amino acid sequence (SEQ ID NO:2) of the wild-type pneumolysin as derived from the DNA sequence of the gene encoding the wild type pneumolysin, FIGS. 4a and 4b show the amino acid sequence (SEQ ID NO:2) of pneumolysin showing amino acid substitutions introduced by site directed mutagenesis, FIG. 5 is a physical map of the pGEMEX-1 vector encoding for mutant pneumolysin, FIG. 6 shows the electrophoresis of the purification run for pneumolysoid, FIG. 7 shows the levels of total immunoglobulin in serum of MF1 mice after various vaccinations, and FIG. 8 shows the levels of anti-PL immunoglobulins of different isotypes in serum of MF1 mice, after vaccination with a certain pneumolysoid.

Recombinant DNA techniques have been used to construct non-toxic pneumolysin derivatives suitable for administration to humans. To achieve this, the *S. pneumoniae* gene encoding pneumolysin was cloned into *Escherichia coli* and its complete DNA sequence determined. The DNA sequence is shown in FIG. 1 and the derived amino acid sequence is shown in FIGS. 3a and 3b.

Three regions of the pneumolysin gene were subjected to oligonucleotide-directed mutagenesis. The first region encodes amino acids 427–437 in the protein sequence, and is indicated by an underline in FIG. 3b. This 11 amino acid sequence shows absolute homology with similar regions in other related thiol activated toxins thus is thought to be responsible for the hemolytic activity and hence toxic activity of the toxin. The other two regions encode amino acids 257–297 and amino acids 368–397 and are also indicated by an underline in FIG. 3b. These two regions of the toxin have substantial amino acid sequence homology with human C-reactive protein (CRP), and by inference therefore, are thought to be responsible for the ability of pneumolysin to bind the Fc region of immunoglobulins and to activate complement. Fifteen separate mutations in the pneumolysin gene, resulting in single amino acid substitutions, were constructed, as shown in FIGS. 4a and 4b. In an effort to maintain the structure of the altered pneumolysin, conservative substitutions were made, so that amino acids are substituted with amino acids of a similar nature.

For the region invoked in hemolytic activity, $Cys_{428} \rightarrow Gly$, $Cys_{428} \rightarrow Ser$, $Trp_{433} \rightarrow Phe$, $Glu_{434} \rightarrow Asp$ and $Trp_{435} \rightarrow Phe$ each reduced hemolytic activity by 97%, 90%, 99%, 75% and 90% respectively. The other mutations in that region $Cys_{428} \rightarrow Ala$, $Glu_{434} \rightarrow Gln$ and $Trp_{436} \rightarrow Phe$ did not affect hemolytic activity. Mutating a separate region of the toxin thought to be responsible for binding to target cell membranes also affects hemolytic activity of the protein. This substitution, $His_{367} \rightarrow Arg$, completely inhibits hemolytic activity. This is a quite unpredictable finding in that $His_{367} \rightarrow Arg$ therefore shows a greater inhibition of this property than the substitutions made within the 11 amino acid region thought to be responsible for hemolytic activity. Mutations in the CRP-like domains were tested for ability to activate complement. For $Trp_{379} \rightarrow Phe$, $Tyr_{384} \rightarrow Phe$, $Asp_{385} \rightarrow Asn$ and $Trp_{397} \rightarrow Phe$, complement activation was reduced by 20%, 70%, 100% and 15%, respectively. The other mutations in the CRP-like domains shown in FIG. 4 do not reduce complement activation.

Importantly, the above mutations which affect either hemolytic activity or complement activation do not impair the immunogenicity of the proteins, compared with native or wild-type pneumolysin.

Thus although $His_{367} \rightarrow Arg$ is the preferred mutation to reduce the hemolytic activity, a combination of two or more mutants effecting reduced hemolytic activity can also achieve a very high level of reduction in hemolytic activity. Similarly $Asp_{385} \rightarrow Asn$ is the preferred mutation to achieve reduced complement activation, however a combination of two or more other mutants that reduce the activity to a lesser degree can also be used.

In a preferred embodiment the pneumolysin derivative for use in the vaccine would contain a combination of certain of the above mutations such that the protein is unable to activate complement in addition to having zero hemolytic activity. Examples of such combination are:

$$His_{367} \rightarrow Arg + Asp_{385} \rightarrow Asn; \quad 1)$$

$$His_{367} \rightarrow Arg + Asp_{385} \rightarrow Asn + either\ Cys_{428} \rightarrow Gly\ or\ Trp_{433} \rightarrow Phe;\ 2)$$

$$Asp_{385} \rightarrow Asn + Cys_{428} \rightarrow Gly + Trp_{433} \rightarrow Phe. \quad 3)$$

These then are some preferred combinations, however it is to be understood that other combinations of mutations can be used to make up the altered pneumolysin for use in a vaccine. Further the altered pneumolysin may comprise any one of the individual mutations with sufficiently reduced activity.

High level expression of the altered pneumolysin from DNA encoding the altered pneumolysin can be achieved by using any one of a number of conventional techniques including the expression in a prokaryotic host with the DNA cloned appropriately within any one of the many expression vectors currently available, or cloned appropriately within the host chromosome; expression in a eukaryotic host with the DNA cloned appropriately either within an expression vector or cloned within the host chromosome; or within an in vitro expression system such as may comprise purified components necessary for expression of altered pneumolysin.

To achieve high level expression of the mutated pneumolysin gene, it has been cloned into the vector pKK233-2 for expression within *Escherichia coli* or other like prokaryote. This vector included ampicillin and tetracycline resistance genes, the trc promoter (which can be regulated by IPTG [isopropyl-B-D-thiogalactopyranosi]), and a lac Z ribosome binding site adjacent to an ATG initiation codon incorporating an NcoI restriction site. Immediately downstream from the initiation codon there are restriction sites for PstI and HindIII, followed by a strong $T_1$ $T_2$ transcription terminator. Prior to insertion into pKK233-2, a NcoI restriction site was constructed at the 5' end of the pneumolysin coding sequence (at the initiation codon) by oligonucleotide-directed mutagenesis, as shown in FIG. 2. This enabled the proximal end of the altered pneumolysin gene to be cloned into the NcoI site of pKK233-2; a HindIII site approximately 80 bases downstream from the pneumolysin termination codon was used to splice the distal end of the altered gene into the compatible site in pKK233-2. The mutant pneumolysin derivative could however, be cloned into any one of a number of high expression vector systems.

The mutant pneumolysin is prepared as follows: *E. coli* cells harboring the above recombinant plasmid are first grown in 9 liter cultures in Luria Bertani (or any other appropriate) medium, supplemented with the appropriate antibiotic, at 37° C., with aeration. When the culture reaches the late logarithmic phase of growth, IPTG is added to a final concentration of 20 $\mu$M (to induce expression of the altered pneumolysin gene) and incubation is continued for a further 2 to 3 hrs.

Cells are then harvested by centrifugation or ultrafiltration and lysed by treatment with EDTA and lysozyme, followed by sonication, or by disruption in a French pressure cell. Cell debris is removed by centrifugation and the extract is then dialyzed extensively against 10 mM sodium phosphate (pH 7.0). The material is then loaded onto a column of DEAE-cellulose and eluted with a linear gradient of 10–250 mM sodium phosphate (pH 7.0). Fractions containing peak levels of the pneumolysin derivative are pooled, concentrated by ultrafiltration and loaded onto a column of Sephacryl S-200. This column is developed in 50 mM sodium phosphate (pH 7.0) and again fractions with high levels of pneumolysin derivative are pooled, concentrated by ultrafiltration and stored in 50% glycerol at –15° C. The final product is greater than 95% pure, as judged by SDS-polyacrylamide gel electrophoresis. Hydrophobic interaction chromatography on Phenyl-Sepharose is an alternative purification which could also be used.

However it is to be understood that this is only one method of purification of the altered pneumolysin, and other, alternative methods (including High Pressure Liquid Chromatography) may be employed. This purified altered pneumolysin can then be administered as a vaccine at appropriate levels, either by itself or in combination with other antigens. In one form, the pneumolysin may be conjugated with polysaccharide derived from any one or more of the variety of pneumococcal strains described above.

The mutant pneumolysin can be conjugated to the various serotypes of polysaccharide by a range of methods. The first involves preparation of an activated polysaccharide by treating pure polysaccharide (available commercially) with cyanogen-bromide and adipicacid dihydrazide (ADH). The ADH-polysaccharide is then combined with the mutant pneumolysin in the presence of 1-ethyl-3-(3-dimethylaminopropyl)carbodiimide-HCl. Conjugated material is separated from the reactants by chromatography through Sepharose CL-4B.

Alternatively, the polysaccharide-mutant pneumolysin conjugates can be prepared using bifunctional reagents such as N-succinimidyl-6(4'azido-2'-nitrophenylamino)hexanoate(SANPAH). Pure polysaccharide dissolved in phosphate buffered saline, is reacted with SANPAH in the presence of a strong white light source. Unreacted SANPAH is then separated from activated polysaccharide by chromatography on Sephadex G-50. Activated polysaccharide is then conjugated to the mutant pneumolysin in 0.2M borate buffer (pH 8.5). Any excess reactive groups are then blocked with lysine, and the polysaccharide-protein conjugate is separated from the other reactants by chromatography on Sepharose CL-4B. Conjugates could also be prepared by reductive amination with cyanoborohydride.

Alternatively another protein, such as inactivated tetanus toxin, can be conjugated with the desired polysaccharides and altered pneumolysin can be added to the vaccine in an unconjugated form. This then describes the best method of performing the invention, however, it is to be understood that the invention is not limited thereto.

DETAILED DESCRIPTION OF THE INVENTION

Cloning of the Pneumolysin Gene

The cloning and DNA sequencing of the pneumolysin gene is described in the paper by Walker et al., 1987, *Infection and Immunity*, 55: 1184–1189). Chromosomal DNA from *Streptococcus pneumoniae* strain D39 (NCTC 7466) was partially restricted with EcoRl and fragments were cloned into bacteriophage λ gt10. Plaques were overlaid with sheep blood agar and hemolytic recombinants selected. The insert DNA from a hemolytic phage was sub-cloned into plasmid by digestion of the recombinant with EcoRl. The lytic product was shown to be pneumolysin as it was completely inhibited by cholesterol and reacted with antiserum raised to the related toxin Streptolysin O. The gene and its flanking DNA were sequenced following shotgun cloning into the sequencing vector M31mp18.

Methods to Prepare Mutants of Pneumolysin

Mutant versions of the pneumolysin gene were constructed by several different methods.

Random Mutagenesis

The pneumolysin gene cloned into M13mp18 was used as a template for base-specific misincorporation mutagenesis using a previously reported technique, that allows single base-specific substitutions throughout genes (Lehtovarra et al., 1988, *Protein Engineering*, 2: 63–68).

Primary Screening Mutants for Reduced Hemolytic Activity

A method was developed to screen the library for clones with reduced or no hemolytic activity. Plaques obtained from the random mutagenesis procedure were picked, using sterile Pasteur pipettes, into 96-well microtiter plates containing 100 µl TES buffer (10 mM Tris HCl pH 8, 1 mM EDTA, 50 mM NACl) in each well. Plates were stored at 4° C. for at least 4 hours to produce a supernatant containing infectious phage particles. An overnight culture of JM101 (Stratagene, La Jolla, Calif.) was diluted 1:100 in fresh LB medium and 150 µl of this solution was added to each well of a microtiter plate. Phage supernatants were transferred to each well using a 48-spike replicator tool. The microtiter plates were incubated overnight at 37° C. without shaking. After overnight growth, a pellet was visible at the bottom of each well. A drop of chloroform was added to each well using the replicator tool. Chloroform addition was repeated twice to ensure lysis of phage-infected cells, and the plates were left at room temperature for 15 mins. Using a multi-channel pipette, 50 µl of supernatant from chloroform-lysed cells was transferred to a fresh microtiter plate, and 50 µl of 2% sheep red blood cells in PBS was added. Plates were then incubated at 37° C. and examined at various times by eye, to determine the extent of hemolysis in each well. The individual clones were ranked for their ability to lyse the red blood cell solution and those displaying least apparent hemolytic activity were selected for further analysis. This screen identified a number of candidates with reduced or no hemolytic activity. The absence or reduction in hemolysis observed might have been due to a single amino acid substitution, as expected. Alteratively, there might have been reduced expression of pneumolysin or poor infectivity of phage. A second screen was therefore developed to eliminate clones that did not produce significant amounts of toxin.

Secondary Screening of Clones

All non-hemolytic clones selected by the primary screen were plaque purified using JM101 as a host strain. JM101, infected with serially diluted phage from microtiter wells, was plated out at several dilutions in soft-top media. Individual plaques were then picked from the appropriate plates that contained well separated plaques. This step determined whether viable phage were present in the microtiter plate well. Four individual plaques were picked for each clone of interest and amplified in JM101. The harvested cells were sonicated and assayed for hemolytic activity. If all, four clones were non-hemolytic, a dot-blot procedure was used to assay for toxin presence in sonicated extracts. Briefly, 5 μl of sonicated cell extracts were spotted onto a nitrocellulose membrane and blocked overnight in 3% skimmed milk in PBS-Tween 20 (PBS-T). Filters were washed in PBS-T, then incubated for 90 mins. with a 1:1000 dilution of rabbit anti-pneumolysin antiserum. Filters were thoroughly washed in PBS-T and incubated for 60 mins. with an IgG-peroxidase conjugate diluted 1:2000 in PBS-T. Filters were washed prior to detection by Enhanced Chemiluminescence (ECL), using methods recommended by the manufacturers (Amersham, UK). Clones that did not produce toxin were eliminated from further studies. Non-hemolytic clones that produced toxin were analyzed by Western blotting, using ECL detection as described above, to ensure a full-length toxin was expressed.

Clones with reduced hemolytic activity were also plaque purified and amplified in JM101. Two-fold serial dilutions of sonicated extracts in PBS were made in microtiter plates. JM101, infected with phage that express wild-type pneumolysin, was used as a standard. An equal volume of 2% sheep red blood cells was added to assess the hemolytic activity in a semi-quantitative manner. Single stranded DNA of clones with less than wild-type hemolytic activity was prepared and sequenced. This method has been published by us (Hill et al., 1994, *Infection and Immunity,* 62: 757–758).

Site-directed Mutagenesis (SDM)

Site directed mutagenesis was done using the method of Kunkel et al., *Methods in Enzymology*, 154: 367–382). M13 phage carrying the pneumolysin gene was passaged through *E. coli* strain RZ1032 which causes the incorporation of uracil in place of thymidine at some positions in the DNA sequence. Mutant oligonucleotides were kinased and annealed to this template. Following extension and ligation of the second strand using T4 DNA ligase and DNA polymerase the mixture was used to transform *E. coli* strain JM101. Parental wild-type sequences, which contain uracil, are degraded in this strain and the newly synthesized mutagenic strand only replicates. Mutants are then selected by sequencing of DNA from resultant plaques. Mutant genes were sequenced in their entirety and subcloned into plasmids for protein expression.

PCR Mutagenesis (1)

Mutants were constructed by splice-extension overlap PCR (Higuchi et al., 1985, *Nucleic Acid Research*, 15:7351). This process uses the fact that sequences added to the 5' end of a PCR primer become incorporated into the product molecule. PCR was used to modify the ends of two fragments of the pneumolysin gene. The modified sequences were designed so that they overlap and were then used in an overlap extension reaction to incorporate the mutation into the appropriate position in the pneumolysin gene.

PCR Mutagenesis (2)

Mutants were constructed by standard PCR amplification of the pneumolysin gene using a mutagenic 3' oligonucleotide.

Preparation of a High Expression Vector Encoding Mutant Pneumolysin

The gene encoding for mutant pneumolysin is inserted immediately downstream from the T7 promoter of the pGEMEX-1 vector utilizing a NdeI site. Therefore a NdeI site was introduced in the initiation codon of the pneumolysin gene by oligonucleotide-directed mutagenesis. For the pGEMEX-1 system, a NdeI site from the vector at position 3251 was removed by deleting a 860 bp SppI fragment (position 2884–3744). This removes the f1 ori region, which is not needed in this construct. A NdeI site is left at position 904 in the initiation codon of the T7 gen. Digestion of the vector with NdeI and SphI removed a further 883 bp of DNA encoding the T7 gene 10 and most of the polylinker region. This enabled insertion of the pneumolysin coding sequence as a 1.5 kb NdeI/SphI fragment into pGEMEX-1. (FIG. 5 shows the physical map of the pGEMEX-1 vector encoding for mutant pneumolysin.)

Expression of Mutated Pneumolysin in *E. coli*

The constructed plasmid was introduced by transformation of the strain *E. coli* JM109. *E. coli* cells bearing plasmids were selected on LB medium containing 50 μg/ml ampicillin. Subsequently the clones were screened for the presence of pneumolysin sequence by dot-blot hybridization to pneumolysin gene probes, and clones expressing intact mutant pneumolysin (pneumolysoid) were detected by Western blot analysis. analysis. Plasmid DNA was also extracted and subjected to restriction analysis to confirm the physical structure.

The transformed cells were then inoculated in 2 bottles (30 ml) each containing 10 ml of LB medium with 50 μg/ml ampicillin and subsequently grown at 37° C. for 3–4 hrs. At the end of this period the 10 ml of each culture were added to 500 ml of fresh LB medium in one liter flasks and were kept under agitation for 3–4 hrs. at 37° C. These cultures were then used to inoculate 2.5 liters of LB medium with ampicillin (50 µg/ml) supplemented with 10 ml of 20% glucose in a New Brunswick Bioflo II fermenter (5 liter capacity vessel). The cells were grown overnight at 37° C. with maximum aeration, agitation at 500 rpm. pH was maintained at 6.8–7.0 with HCl or $NH_4OH$. Next morning one liter LB medium with 50 µg/ml ampicillin, 20 ml 20% (w/v) glucose as well as 200 mg isopropyl-β-thiogalactoside were added. The culture was continued for another 2 h. The cultures were centrifuged and the cells separated and resuspended in 70 ml of 10 mM sodiumphosphate pH 7.0.

Purification of Mutated Pneumolysin

The said cell suspension was then lysed by passage through a French pressure cell at 15,000 psi. The cell lysate was centrifuged at 35,000×g for 20 mins. at 4° C. The supernatant was separated and centrifuged at 150,000×g for 60 mins. at 4° C. The supernatant containing soluble pneumolysoid was used for purification.

The crude supernatant was loaded onto a DEAE Sepharose CL-6B column (5 cm×60 cm) at 4° C. The column was eluted with a 2 liter linear gradient of 10–250 mM sodiumphosphate pH 7.0 applied at a flow rate of 100 ml/h. The column effluent was collected in fractions of 20 ml. Fractions containing detoxified pneumolysin were identified by a sandwich ELISA using rabbit anti-pneumolysin serum and mouse anti-pneumolysin monoclonal or a dot-blot immunoassay using rabbit anti-pneumolysin. Peak fractions containing pneumolysoid were pooled and concentrated by ultrafiltration using an Amicon 250 ml capacity stirred cell with an YM10 (10,000 MW cut off) membrane. The partially purified pneumolysoid is then loaded onto a Sephacryl S200 HR column (2.6×100 cm). The column was equilibrated and eluted with 50 mM sodiumphosphate pH 7.0 at a flow rate of 30 ml/h. Fractions of 10 ml were collected and assayed as before. Peak fractions containing detoxified pneumolysin were concentrated by ultrafiltration up to a maximum of 5 mg/ml. The yield was 30–50 mg with a purity estimated with SDS-PAGE to be 90–95% The purified pneumolysoid is then supplemented to 50% glycerol and stored at −15° C.

Various samples were taken during purification of pneumolysoid and subjected to electrophoresis. FIG. 6 shows the results of the electrophoresis, in which Lane 1 contains molecular weight markers 97.4, 66.2, 45.0, 31.0 and 21.0 kDa from top to bottom, Lane 2 contains crude *E. coli* lysate, Lane 3 contains post DEAE Sepharose CL-6B, and Lane 4 contains post Sephacryl S200HR. Ten µl of samples taken during purification had added 0.05% bromophenol blue, 5% β-mercaptoethanol, 10% glycerol, they were brought to boiling point for five mins. and then loaded onto a 12.5% polyacrylamide gel. The proteins were then subjected to electrophoresis at 200 V for 3 hrs. and the gel was colored and decolored as reported by Laemli (Nature 227, 680–685).

In vitro Characterization of Mutant Pneumolysin

Hemolytic Activity

Doubling dilutions (50 µl) of toxin solution are added to an equal volume of sheep red blood cells. That dilution which causes lysis of 50% of the cells is taken as the end point. The reciprocal of this dilution is taken as the number of hemolytic units. This value is normalized for the concentration of the toxin and is expressed as hemolytic units per milligram of protein.

Complement Activation

10 µg of toxin was incubated in normal human serum at 37° C. for 30 mins. Complement activation was measured by using two-dimensional immunoelectrophoresis to visualize the C3b released (Mitchell et al., 1989, *Biochim. Biophys. Acta*, 1007:67–72).

Cell Binding

Dilutions of the toxin, from 260 to 3 ng/ml, were made in 3 ml of Hanks buffered salts solution (HBSS) containing 0.2% (v/v) sheep erythrocytes and incubated in an ice-water bath for 30 mins. The cells were washed three times in ice-cold HBSS, then lysed in water. The membranes were harvested and washed twice in water by centrifugation at 13,000 rpm in a microfuge and then resuspended in sodium dodecyl sulphate-polyacrylamidegel electrophoresis (SDS-PA-GE) loading buffer. SDS-PAGE was done and the proteins were transferred to nitrocellulose membranes. The membranes were incubated in 5% (w/v) skimmed milk powder in PBS for 60 mins., washed in PBS and incubated with rabbit anti-pneumolysin antiserum, diluted 1/1000 in PBS, for 90 mins. The membranes were washed, incubated for 60 mins. in 1/2000 goat anti-rabbit antiserum and then extensively washed in PBS. The proteins recognized by the anti-pneumolysin antiserum were visualized using Enhanced Chemiluminescence reagents (Amersham) following the manufacturer's instructions. The results were quantified using an LKB Ultrascan XL densitometer.

Data on the in vitro biological activity of mutants of pneumolysin are presented in Table 1.

Thus, the data in Table 1 illustrates that the present invention provides substantially reduced hemolytic activity and reduced complement bonding activity as compared to wild-type pneumolysins.

In vivo Characterization of Mutant Pneumolysin ($Trp_{433}$→Phe)

Preparation of Anti-pneumolysin Serum

New Zealand white rabbits were injected with 10 μg of purified pneumolysin in Freund's complete adjuvant intramuscularly three times at three week intervals. Three weeks after the final intramuscular injection rabbits were boosted with 10 μg of pneumolysin intravenously and were bled from the ear vein one week later.

Analysis of Serum Response to Immunization with Detoxified Mutant Pneumolysin ($Trp_{133}$→Phe Female MFl mice (Harlan, Olac Ltd.) weighing 30–35 g were injected intraperitoneally with 20 μg of purified pneumolysoid. One group of mice were immunized with 0.1 ml phosphate buffered saline, 50% v/v glycerol, emulsified with 0.1 ml Freund's complete adjuvant (Sigma Chemical Co. Poole, UK). At 10-day intervals the mice were given two additional injections of 20 μg of purified mutant pneumolysin in PBS, 50% v/v glycerol, emulsified with Freund's incomplete adjuvant (Sigma, Poole, UK). Another group of mice was injected intraperitoneally with 20 μg of purified pneumolysin adsorbed to aluminum phosphate. At 10-day intervals the mice were given two additional injections. As a control for each of these two groups of mice, groups of mice were immunized according to the same protocol with adjuvant only. Blood samples were taken from the tail vein before each injection and before challenge. Sera were stored at −20° C. until use. Sera from mice in which aluminum phosphate was used as the adjuvant were assayed for the presence of anti-pneumolysin antibodies in ELISA. The results expressed as average from 10 animals tested individually are reported in FIG. 7. In FIG. 7, the solid line represents the mice vaccinated with the pneumolysin in alum adjuvant (aluminum phosphate), the dotted line represents the pneumolysoid in Freunds adjuvant, and the dashed line represents the control using PBS adjuvant only. Each point represents the arithmetic mean of ten mice, and the bars represent the standard error of the mean.

The sera from mice immunized with toxoid and Freunds adjuvant were analyzed from their isotypes profile. The results (FIG. 8) showed that the major isotypes present were IgG1 and IgG2. In FIG. 8, each column represents the arithmetic mean of ten mice, and the bars represent the standard error of the mean.

Intranasal Challenge with Various Pneumococcal Serotypes after Immunization with Mutant Pneumolysin Preparation of a Standard Pneumococcal Inoculum Pneumococcal strains (supplied by RIVM, clinical isolates from Leicester Royal Infirmary or purchased from NCTC) were inoculated into brain heart infusion broth (BHI, Oxoid) and grown up overnight. 100 µl of the overnight culture were injected intraperitoneally into an MFI mouse. Organisms were recovered from the mouse by plating a blood sample taken from the tail vein 24 hrs. later onto blood agar base (BAB, Oxoid) containing 5% (v/v) horse blood. Plates were incubated overnight at 37° C. Four-five colonies were then inoculated in bottles each containing 10 ml of brain-heart infusion broth (BHI) and were grown overnight at 37° C. Next morning the culture was centrifuged, the pellet was separated and resuspended in 1 ml of BHI supplemented with 17% (v/v) fetal calf serum (FCS). The bacterial suspension was diluted with fresh medium up to OD of 0.7 was reached. This culture was then incubated at 37° C. for 4–5 hrs. The number of viable cells were estimated by plating the bacteria on BAB+5% horse blood in triplicate and incubating the plates overnight at 37° C. The remainder of the culture was frozen at −20° C. Next day the cells were thawed and diluted with BHI+FCS to a concentration of $2 \times 10^7$ cfu per ml aliquoted in 1 ml portions and stored at −70° C. until use. When required, the suspension was thawed slowly at room temperature and bacteria were harvested by centrifugation before resuspension to the required concentration in sterile PBS.

Intranasal Challenge

Female MFI mice, weighing approximately 30–35 g, were immunized with mutant pneumolysin as described above using aluminum phosphate as the adjuvant.

One month after the third injection, mice were lightly anesthetized with 80 µl of 1 mg/ml Hypnorm (Janssen) given intraperitoneally. Twenty minutes after administration of the anaesthetic, mice were challenged with 50 µl of PBS containing the number of colony forming units of S. pneumoniae strains (see Table 2), which caused the control mice to become moribund in approximately 3 days, administered in the nostrils. Challenged mice were kept warm until they had recovered consciousness (2–3 hrs.) The mice were monitored for visible clinical symptoms for 14 days, at which the experiment was ended. Mice that were alive at this point were considered to have survived the pneumococcal challenge. Mice that became moribund was recorded and the animal was killed humanely. The survival time of each mouse is given in Table 2. The results given in this table indicate that a significant increase in the survival times of immunized mice was seen in each case except for type 3 strain GBO5.

Intraperitoneal Challenge with Various Pneumococcal Serotypes of Mice Repeatedly Immunized with Mutant Pneumolysin Preparation of a Standard Pneumococcal Inoculum Pneumococcal strains stored at −80° C. in serum broth (meat extract broth+10% horse serum) was used to inoculate a blood agar plate. Plates were incubated overnight at 37° C. After that one loop of cells was suspended in 3 ml of serum broth. The culture was incubated at 37° C. until an $OD_{600}$ of 0.2 corresponding with $1.0 \times 10^8$ cfu/ml. The culture was diluted in serum broth, as appropriate immediately prior to intraperitoneal challenge.

Intraperitoneal Challenge

Male and female Quackenbush strain (Q/S) mice, 6–8 weeks old, were injected subcutaneously with 0.1 ml volumes of a 20% suspension of alum adjuvant (Imjcet Alum, Pierce, Rockford, Ill.) in PBS, containing 20 µg of mutant pneumolysin. Mice in control groups received 0.1 ml of a suspension of 20% alum and PBS. At 14 day intervals mice were given additional injections. Two weeks after the third injection mice were challenged intraperitoneally with a 0.1 ml dose of pneumococci calculated to represent approximately 20 times the 50% lethal dose for each strain. The time of death of mice over the subsequent 14 day period was recorded. The experiment was ended after 14 days and mice alive at this time were recorded as survivors.

Groups of 15 immunized and non-immunized Q/S mice were challenged intraperitoneally with the dose of each strain of pneumococcus shown in Table 3. The survival times of the mice was recorded and is presented in Table 3. The results indicate that the survival times of the mice immunized with mutant pneumolysin were significantly increased with respect to those of the control mice with each of the eight challenge strains of pneumococcus.

Parenteral Vaccine Preparation

5–50 g of the mutant pneumolysin is mixed with an aluminum adjuvant such as aluminum phosphate, to produce a vaccine in a form appropriate for incorporation into a parenteral administration dosage form.

The vaccine of the invention may be prepared as a pharmaceutical composition containing an immunoprotective, non toxic amount of the protein of the invention in a non toxic and sterile pharmaceutically acceptable carrier. The mode of administration of the vaccine of the invention may be any suitable route which delivers protection to infection with virulent pneumococci. Where the vaccine is administered parenterally, via the intramuscular or deep subcutaneous route, the protein can be optionally admixed or absorbed with any conventional adjuvant to attract or to enhance the immune response. Such adjuvants include but are not restricted to aluminum hydroxide, aluminum phosphate, muramyl dipeptide, bacterial lipopolysaccharides and derivatives and purified saponins from Quil A. The protein can also be presented to the immune system within microparticles such as liposomes or ISCOMs. A vaccine formulation containing the protein of the invention may be designed for oral or intranasal ingestion.

The therapeutically effective and non toxic dose of the vaccine can be determined by skill in the art. However the specific dose for any person will depend upon a variety of factors including age, general health, diet of the patient, time and route of administration, synergistic effects with other drugs being administered and whether the vaccine is administered repeatedly. If necessary the vaccine will be administered repeatedly with one to three month intervals between each dose and with an optional booster dose later in time.

TABLE 1

Data on the in vitro biological activity of mutants of pneumolysin.

| pneumolysin mutant | haemolytic activity (%) | complement activity (%) | cell binding (%) | Method used to construct mutant |
|---|---|---|---|---|
| Arg31 -->Cys | 75 | ND | ND | RANDOM |
| Leu75 -->Phe | 100 | ND | ND | RANDOM |
| Val127 -->Gly | 75 | ND | ND | RANDOM |
| His156 -->Tyr | 0.1 | ND | ND | RANDOM |
| His367 -->Arg | 0.1 | ND | ND | RANDOM |
| Asp385 -->Asn | 100 | <1 | 100 | SDM |
| His386 -->Arg | 10 | ND | ND | PCR(1) |
| Glu390 -->Asp | | | | |
| Cys428 -->Ala | 100 | 100 | 100 | SDM |
| Cys428 -->Gly | 1 | 100 | 100 | SDM |
| Cys428 -->Ser | 10 | 100 | 100 | SDM |
| Ala432 -->Val | 100 | ND | ND | RANDOM |
| Trp433 -->Arg | 0.01 | ND | ND | RANDOM |
| Trp433 -->Phe | 0.1 | 100 | 100 | SDM |
| Glu434 -->Gln | 20 | 100 | 100 | SDM |
| Glu434 -->Asp | 50 | 100 | 100 | SDM |
| Trp435 -->Phe | 10 | 100 | 100 | SDM |
| Trp436 -->Phe | 100 | 100 | 100 | SDM |
| Trp436 -->Arg | 50 | ND | ND | RANDOM |
| Pro462 -->Ser | 25 | ND | 10 | PCR(2) |
| Asp385 -->Asn Cys428 -->Gly | 10 | ND | ND | Cloning |
| His156 -->Tyr Asp385 -->Asn | 0.1 | ND | ND | Cloning |
| His156 -->Tyr Asp385 -->Asn Trp433 -->Phe | <0.001 | ND | ND | |
| Trp433 -->Phe Asp385 -->Asn | 0.5 | ND | ND | SDM |
| His367 -->Arg Asp385 -->Asn | 0.1 | ND | ND | Cloning |
| His367 -->Arg Asp385 -->Asn Trp433 -->Phe | 0 | ND | ND | Cloning |

ND = Not done
Note: Data are presented as compared to native pneumolysine (%).

TABLE 2

Protection of mice against intraperitoneal challenge with various S. pneumoniae strains elicited by immunization with PdB.

| | | | Survival Time (days) | | | % Survival | | |
|---|---|---|---|---|---|---|---|---|
| Type | HU[a] | Dose[b] | Control | Immune | p[c] | Control | Immune | p[d] |
| 1 | 621 | $1 \times 10^7$ | 5.1 | >14 | <0.001 | 13 | 60 | <0.005 |
| 3 | 335 | $1 \times 10^5$ | 3.0 | 3.8 | <0.025 | 13 | 0 | NS |
| 4 | 585 | $4 \times 10^3$ | 1.8 | >14 | <0.003 | 7 | 73 | <0.0005 |
| 5 | 693 | $2 \times 10^8$ | 5.5 | 9.3 | <0.005 | 15 | 36 | NS |
| 6 | 424 | $1 \times 10^7$ | 3.9 | >14 | <0.001 | 7 | 67 | <0.005 |
| 7F | 221 | $2 \times 10^7$ | 1.8 | 7.9 | <0.05 | 20 | 33 | NS |
| 8 | 23 | $4 \times 10^3$ | 1.2 | 1.5 | <0.003 | 0 | 7 | NS |
| 18C | 330 | $1 \times 10^5$ | 1.8 | 2.3 | <0.03 | 0 | 14 | NS |

[a]Pneumolysin production expressed as HU per ml culture at $A_{600} = 1.0$.
[b]Challenge dose in number of colony forming units
[c]Significance of difference, Mann-Whitney U-test
[d]Significance of difference, $\chi^2$ test

TABLE 3

Protection of mice against intranasal challenge with various S. pneumoniae strains elicited by immunization with PdB.

| | | | Survival Time (days) | | | % Survival | | |
|---|---|---|---|---|---|---|---|---|
| Type | HU/ml[a] | Dose[b] | Control | Immune | p[c] | Control | Immune | p[d] |
| 1N | 160 | $4.0 \times 10^6$ | 3.0 | 3.9 | <0.05 | 10 | 40 | <0.01 |
| 2 | 640 | $1.0 \times 10^6$ | 3.2 | >14.0 | <0.01 | 6 | 72 | <0.01 |
| 3 | 320 | $1.0 \times 10^6$ | 2.8 | 4.0 | <0.01 | 10 | 33 | <0.01 |
| 7F | 140 | $2.0 \times 10^6$ | 2.9 | >14.0 | <0.01 | 0 | 70 | <0.01 |
| 18C | 260 | $1.0 \times 10^7$ | 3.2 | >14.0 | <0.01 | 5 | 85 | <0.01 |

[a]One hemolytic unit (HU) is defined as the amount of pneumolysin that causes 50% hemolysis of 1% sheep erythrocytes when incubated at 37° C. for 30 min.
[b]Challenge dose in number of colony forming units
[c]Significance of difference, Mann-Whitney U-test
[d]Significance of difference, $\chi^2$ test

What is claimed is:

1. An altered and purified pneumolysin being substantially non-toxic and being capable of eliciting a protective immune response against pneumococcal bacteria in an animal, comprising the polypeptide of SEQ ID: 2 with one to three amino acid substitutions in at least one of the regions 257–297, 367–397 and 427–437.

2. A composition for eliciting an immune response against pneumococcal bacteria in an animal, comprising an adjuvant and the altered and purified pneumolysin according to claim 1.

3. An altered and purified pneumolysin being substantially non-toxic and being capable of eliciting a protective immune response against pneumococcal bacteria in an animal, comprising the polypeptide of SEQ ID: 2 with one to three amino acid substitutions in at least one of the regions 257–297, 367–397 and 427–437, wherein said amino acid substitution is selected from the group consisting of: $His_{367} \rightarrow Arg$; $Cys_{428} \rightarrow Gly$; $Cys_{428} \rightarrow Ser$; $Trp_{433} \rightarrow Phe$; $Glu_{434} \rightarrow Gln$; $Trp_{435} \rightarrow Phe$; a combination of $Asp_{385} \rightarrow Asn$ and $Cys_{428} \rightarrow Gly$; a combination of $Trp_{433} \rightarrow Phe$ and $Asp_{385} \rightarrow Asn$; a combination of $His_{367} \rightarrow Arg$ and $Asp_{385} \rightarrow Asn$; and a combination of $His_{367} \rightarrow Arg$, $Asp_{385} \rightarrow Asn$ and $Trp_{433} \rightarrow Phe$.

4. An altered and purified pneumolysin being substantially non-toxic and being capable of eliciting a protective immune response against pneumococcal bacteria in an animal, comprising the polypeptide of SEQ ID NO: 2 with one to three amino acid substitutions, a said amino acid substitution being of $His_{156}$ in SEQ ID NO: 2.

5. A composition for eliciting an immune response against pneumococcal bacteria in an animal, comprising an adjuvant and the altered and purified pneumolysin according to claim 4.

6. An altered and purified pneumolysin being substantially non-toxic and being capable of eliciting a protective immune response against pneumococcal bacteria in an animal, comprising the polypeptide of SEQ ID NO: 2 with one to three amino acid substitutions, a said amino acid substitution being of $His_{156}$ in SEQ ID NO: 2, wherein said at least one amino acid substitution is selected from the group consisting of: $His_{156} \rightarrow Tyr$; a combination of $His_{156} \rightarrow Tyr$ and $Asp_{385} \rightarrow Asn$; and a combination of $His_{156} \rightarrow Tyr$, $Asp_{385} \rightarrow Asn$ and $Trp_{433} \rightarrow Phe$.

7. An altered and purified pneumolysin being substantially non-toxic and being capable of eliciting a protective immune response against pneumococcal bacteria in an animal, comprising the polypeptide of SEQ ID NO: 2 with one to three amino acid substitutions, a said amino acid substitution being of $His_{156}$ in SEQ ID NO: 2, and further comprising an amino acid substitution in at least one of the regions 257–297, 367–397 and 427–437 of SEQ ID NO: 2.

8. An altered and purified pneumolysin having reduced haemolytic activity relative to wild-type pneumolysin and being capable of eliciting a protective immune response against pneumococcal bacteria in an animal comprising a polypeptide of SEQ ID NO: 2 with one to three amino acid substitutions in one of the regions 257–297, 367–397 and 427–437.

9. An altered and purified pneumolysin having reduced haemoltyic activity relative to wild-type pneumolysin and reduced complement binding activity relative to wild-type pneumolysin and being capable of eliciting a protective immune response against pneumococcal bacteria in an animal, comprising a polypeptide of SEQ ID NO: 2 with one to three amino acid substitutions in at least one of the regions 257–297, 367–397 and 427–437.

10. An altered and purified pneumolysin having reduced haemolytic activity relative to wild-type pneumolysin and being capable of eliciting a protective immune response against pneumococcal bacteria in an animal comprising a polypeptide of SEQ ID NO: 2 with one to three amino acid substitutions in one of three regions 257–297, 367–397 and 427–437, wherein one of said amino acid substitutions is $Trp_{435} \rightarrow Phe$.

11. An altered and purified pneumolysin having reduced haemolytic activity relative to wild-type pneumolysin and being capable of eliciting a protective immune response against pneumococcal bacteria in an animal comprising a polypeptide of SEQ ID NO: 2 with one to three amino acid substitutions in one of three regions 257–297, 367–397 and 427–437, wherein said amino acid substitutions comprise $Trp_{433} \rightarrow Phe$ and $Asp_{385} \rightarrow Asn$.

12. An altered and purified pneumolysin being substantially non-toxic and being capable of eliciting a protective immune response against pneumococcal bacteria in an animal, comprising the polypeptide of SEQ ID NO: 2 with one to three amino acid substitutions in at least one of the regions 257–297, 367–397 and 427–437, wherein one of said amino acid substitutions is $His_{367} \rightarrow Arg$.

13. An altered and purified pneumolysin being substantially non-toxic and being capable of eliciting a protective immune response against pneumococcal bacteria in an animal, comprising the polypeptide of SEQ ID NO: 2 with one to three acid substitutions in at least one of the regions 257–297, 367–397 and 427–437, wherein one of said amino acid substitutions is $Cys_{428} \rightarrow Gly$.

14. An altered and purified pneumolysin being substantially non-toxic and being capable of eliciting a protective immune response against pneumococcal bacteria in an animal, comprising the polypeptide of SEQ ID NO: 2 with one to three amino acid substitutions in at least one of the regions 257–297, 367–397 and 427–437, wherein one of said amino acid substitutions is $Cys_{428} \rightarrow Ser$.

15. An altered and purified pneumolysin being substantially non-toxic and being capable of eliciting a protective immune response against pneumococcal bacteria in an animal, comprising the polypeptide of SEQ ID NO: 2 with one to three amino acid substitutions in at least one of the regions 257–297, 367–397 and 427–437, wherein one of said amino acid substitutions is $Glu_{434} \rightarrow Gln$.

16. An altered and purified pneumolysin being substantially non-toxic and being capable of eliciting a protective immune response against pneumococcal bacteria in an animal, comprising the polypeptide of SEQ ID NO:2 with one to three amino acid substitutions in at least one of the regions 257–297, 367–397 and 427–437, wherein one of said amino acid substitutions is $Trp_{435} \rightarrow Phe$.

17. An altered and purified pneumolysin being substantially non-toxic and being capable of eliciting a protective immune response against pneumococcal bacteria in an animal, comprising the polypeptide of SEQ ID NO: 2 with one to three amino acid substitutions in at least one of the regions 257–297, 367–397 and 427–437, wherein said amino acid substitutions comprise $Asp_{385} \rightarrow Asn$ and $Cys_{428} \rightarrow Gly$.

18. An altered and purified pneumolysin being substantially non-toxic and being capable of eliciting a protective immune response against pneumococcal bacteria in an animal, comprising the polypeptide of SEQ ID NO:2 with one to three amino acid substitutions in at least one of the regions 257–297, 367–397 and 427–437, wherein one of said amino acid substitutions comprises $Trp_{433} \rightarrow Phe$ and $Asp_{385} \rightarrow Asn$.

19. An altered and purified pneumolysin being substantially non-toxic and being capable of eliciting a protective immune response against pneumococcal bacteria in an animal, comprising the polypeptide of SEQ ID NO:2 with one to three amino acid substitutions in at least one of the regions 257–297, 367–397 and 427–437, wherein said one to three amino acid substitutions comprise $His_{367} \rightarrow Arg$ and $Asp_{385} \rightarrow Asn$.

20. An altered and purified pneumolysin being substantially non-toxic and being capable of eliciting a protective immune response against pneumococcal bacteria in an animal, comprising the polypeptide of SEQ ID NO: 2 with one to three amino acid substitutions, a said amino acid substitution being $His_{156}$ in SEQ ID NO:2, and wherein said one to three amino acid substitutions comprise $His_{156} \rightarrow Tyr$ and $Asp_{385} \rightarrow Asn$.

21. An altered and purified pneumolysin being substantially non-toxic and being capable of eliciting a protective immune response against pneumococcal bacteria in an animal, comprising the polypeptide of SEQ ID NO:2 with one to three amino acid substitutions, a said amino acid substitution being $His_{156}$ in SEQ ID NO:2, and wherein said one to three amino acid substitutions comprise $His_{156} \rightarrow Tyr$; $Asp_{385} \rightarrow Asn$ and $Trp_{433} \rightarrow Phe$.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1415 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 3..1415

(xi) SEQUENCE DESCRIPTION: SEQ ID NO:1:

```
AG ATG GCA AAT AAA GCA GTA AAT GAC TTT ATA CTA GCT ATG AAT TAC     47
   Met Ala Asn Lys Ala Val Asn Asp Phe Ile Leu Ala Met Asn Tyr
   1               5                  10                  15
```

-continued

```
GAT AAA AAG AAA CTC TTG ACC CAT CAG GGA GAA AGT ATT GAA AAT CGT         95
Asp Lys Lys Lys Leu Leu Thr His Gln Gly Glu Ser Ile Glu Asn Arg
            20                  25                  30

TTC ATC AAA GAG GGT AAT CAG CTA CCC GAT GAG TTT GTT GTT ATC GAA        143
Phe Ile Lys Glu Gly Asn Gln Leu Pro Asp Glu Phe Val Val Ile Glu
        35                  40                  45

AGA AAG AAG CGG AGC TTG TCG ACA AAT ACA AGT GAT ATT TCT GTA ACA        191
Arg Lys Lys Arg Ser Leu Ser Thr Asn Thr Ser Asp Ile Ser Val Thr
    50                  55                  60

GCT ACC AAC GAC AGT CGC CTC TAT CCT GGA GCA CTT CTC GTA GTG GAT        239
Ala Thr Asn Asp Ser Arg Leu Tyr Pro Gly Ala Leu Leu Val Val Asp
65                  70                  75

GAG ACC TTG TTA GAG AAT AAT CCC ACT CTT CTT GCG GTT GAT CGT GCT        287
Glu Thr Leu Leu Glu Asn Asn Pro Thr Leu Leu Ala Val Asp Arg Ala
 80                  85                  90                  95

CCG ATG ACT TAT AGT ATT GAT TTG CCT GGT TTG GCA AGT AGC GAT AGC        335
Pro Met Thr Tyr Ser Ile Asp Leu Pro Gly Leu Ala Ser Ser Asp Ser
                100                 105                 110

TTT CTC CAA GTG GAA GAC CCC AGC AAT TCA AGT GTT CGC GGA GCG GTA        383
Phe Leu Gln Val Glu Asp Pro Ser Asn Ser Ser Val Arg Gly Ala Val
            115                 120                 125

AAC GAT TTG TTG GCT AAG TGG CAT CAA GAT TAT GGT CAG GTC AAT AAT        431
Asn Asp Leu Leu Ala Lys Trp His Gln Asp Tyr Gly Gln Val Asn Asn
        130                 135                 140

GTC CCA GCT AGA ATG CAG TAT GAA AAA ATA ACG GCT CAC AGC ATG GAA        479
Val Pro Ala Arg Met Gln Tyr Glu Lys Ile Thr Ala His Ser Met Glu
    145                 150                 155

CAA CTC AAG GTC AAG TTT GGT TCT GAC TTT GAA AAG ACA GGG AAT TCT        527
Gln Leu Lys Val Lys Phe Gly Ser Asp Phe Glu Lys Thr Gly Asn Ser
160                 165                 170                 175

CTT GAT ATT GAT TTT AAC TCT GTC CAT TCA GGT GAA AAG CAG ATT CAG        575
Leu Asp Ile Asp Phe Asn Ser Val His Ser Gly Glu Lys Gln Ile Gln
                180                 185                 190

ATT GTT AAT TTT AAG CAG ATT TAT TAT ACA GTC AGC GTA GAC GCT GTT        623
Ile Val Asn Phe Lys Gln Ile Tyr Tyr Thr Val Ser Val Asp Ala Val
            195                 200                 205

AAA AAT CCA GGA GAT GTG TTT CAA GAT ACT GTA ACG GTA GAG GAT TTA        671
Lys Asn Pro Gly Asp Val Phe Gln Asp Thr Val Thr Val Glu Asp Leu
        210                 215                 220

AAA CAG AGA GGA ATT TCT GCA GAG CGT CCT TTG GTC TAT ATT TCG AGT        719
Lys Gln Arg Gly Ile Ser Ala Glu Arg Pro Leu Val Tyr Ile Ser Ser
    225                 230                 235

GTT GCT TAT GGG CGC CAA GTC TAT CTC AAG TTG GAA ACC ACG AGT AAG        767
Val Ala Tyr Gly Arg Gln Val Tyr Leu Lys Leu Glu Thr Thr Ser Lys
240                 245                 250                 255

AGT GAT GAA GTA GAG GCT GCT TTT GAA GCT TTG ATA AAA GGA GTC AAG        815
Ser Asp Glu Val Glu Ala Ala Phe Glu Ala Leu Ile Lys Gly Val Lys
                260                 265                 270

GTA GCT CCT CAG ACA GAG TGG AAG CAG ATT TTG GAC AAT ACA GAA GTG        863
Val Ala Pro Gln Thr Glu Trp Lys Gln Ile Leu Asp Asn Thr Glu Val
            275                 280                 285

AAG GCG GTT ATT TTA GGG GGC GAC CCA AGT TCG GGT GCC CGA GTT GTA        911
Lys Ala Val Ile Leu Gly Gly Asp Pro Ser Ser Gly Ala Arg Val Val
        290                 295                 300

ACA GGC AAG GTG GAT ATG GTA GAG GAC TTG ATT CAA GAA GGC AGT CGC        959
Thr Gly Lys Val Asp Met Val Glu Asp Leu Ile Gln Glu Gly Ser Arg
    305                 310                 315

TTT ACA GCA GAT CAT CCA GGC TTG CCG ATT TCC TAT ACA ACT TCT TTT       1007
Phe Thr Ala Asp His Pro Gly Leu Pro Ile Ser Tyr Thr Thr Ser Phe
```

```
                320                 325                 330                 335
TTA CGT GAC AAT GTA GTT GCG ACC TTT CAA AAC AGT ACA GAC TAT GTT    1055
Leu Arg Asp Asn Val Val Ala Thr Phe Gln Asn Ser Thr Asp Tyr Val
                    340                 345                 350

GAG ACT AAG GTT ACA GCT TAC AGA AAC GGA GAT TTA CTG CTG GAT CAT    1103
Glu Thr Lys Val Thr Ala Tyr Arg Asn Gly Asp Leu Leu Leu Asp His
                355                 360                 365

AGT GGT GCC TAT GTT GCC CAA TAT TAT ATT ACT TGG GAT GAA TTA TCC    1151
Ser Gly Ala Tyr Val Ala Gln Tyr Tyr Ile Thr Trp Asp Glu Leu Ser
            370                 375                 380

TAT GAT CAT CAA GGT AAG GAA GTC TTG ACT CCT AAG GCT TGG GAC AGA    1199
Tyr Asp His Gln Gly Lys Glu Val Leu Thr Pro Lys Ala Trp Asp Arg
        385                 390                 395

AAT GGG CAG GAT TTG ACG GCT CAC TTT ACC ACT AGT ATT CCT TTA AAA    1247
Asn Gly Gln Asp Leu Thr Ala His Phe Thr Thr Ser Ile Pro Leu Lys
400                 405                 410                 415

GGG AAT GTT CGT AAT CTC TCT GTC AAA ATT AGA GAG TGT ACC GGG CTT    1295
Gly Asn Val Arg Asn Leu Ser Val Lys Ile Arg Glu Cys Thr Gly Leu
                420                 425                 430

GCC TGG GAA TGG TGG CGT ACG GTT TAT GAA AAA ACC GAT TTG CCA CTA    1343
Ala Trp Glu Trp Trp Arg Thr Val Tyr Glu Lys Thr Asp Leu Pro Leu
                    435                 440                 445

GTG CGT AAG CGG ACG ATT TCT ATT TGG GGA ACA ACT CTC TAT CCT CAG    1391
Val Arg Lys Arg Thr Ile Ser Ile Trp Gly Thr Thr Leu Tyr Pro Gln
                450                 455                 460

GTA GAG GAT AAG GTA GAA AAT GAC                                    1415
Val Glu Asp Lys Val Glu Asn Asp
        465                 470

(2) INFORMATION FOR SEQ ID NO:2:

(i) SEQUENCE CHARACTERISTICS:
        (A) LENGTH: 471 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160
```

```
Leu Lys Val Lys Phe Gly Ser Asp Phe Glu Lys Thr Gly Asn Ser Leu
            165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
            210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
            290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
            325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
            370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
            450                 455                 460

Glu Asp Lys Val Glu Asn Asp
465                 470
```

(2) INFORMATION FOR SEQ ID NO:3:

(i) SEQUENCE CHARACTERISTICS:
        (A) LENGTH: 1415 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
CCATGGCAAA TAAAGCAGTA AATGACTTTA TACTAGCTAT GAATTACGAT AAAAAGAAAC    60

TCTTGACCCA TCAGGGAGAA AGTATTGAAA ATCGTTTCAT CAAAGAGGGT AATCAGCTAC   120

CCGATGAGTT TGTTGTTATC GAAAGAAAGA AGCGGAGCTT GTCGACAAAT ACAAGTGATA   180
```

-continued

```
TTTCTGTAAC AGCTACCAAC GACAGTCGCC TCTATCCTGG AGCACTTCTC GTAGTGGATG    240

AGACCTTGTT AGAGAATAAT CCCACTCTTC TTGCGGTTGA TCGTGCTCCG ATGACTTATA    300

GTATTGATTT GCCTGGTTTG GCAAGTAGCG ATAGCTTTCT CCAAGTGGAA GACCCCAGCA    360

ATTCAAGTGT TCGCGGAGCG GTAAACGATT TGTTGGCTAA GTGGCATCAA GATTATGGTC    420

AGGTCAATAA TGTCCCAGCT AGAATGCAGT ATGAAAAAAT AACGGCTCAC AGCATGGAAC    480

AACTCAAGGT CAAGTTTGGT TCTGACTTTG AAAAGACAGG GAATTCTCTT GATATTGATT    540

TTAACTCTGT CCATTCAGGT GAAAAGCAGA TTCAGATTGT TAATTTTAAG CAGATTTATT    600

ATACAGTCAG CGTAGACGCT GTTAAAAATC CAGGAGATGT GTTTCAAGAT ACTGTAACGG    660

TAGAGGATTT AAAACAGAGA GGAATTTCTG CAGAGCGTCC TTTGGTCTAT ATTTCGAGTG    720

TTGCTTATGG GCGCCAAGTC TATCTCAAGT TGGAAACCAC GAGTAAGAGT GATGAAGTAG    780

AGGCTGCTTT TGAAGCTTTG ATAAAAGGAG TCAAGGTAGC TCCTCAGACA GAGTGGAAGC    840

AGATTTTGGA CAATACAGAA GTGAAGGCGG TTATTTTAGG GGGCGACCCA AGTTCGGGTG    900

CCCGAGTTGT AACAGGCAAG GTGGATATGG TAGAGGACTT GATTCAAGAA GGCAGTCGCT    960

TTACAGCAGA TCATCCAGGC TTGCCGATTT CCTATACAAC TTCTTTTTTA CGTGACAATG   1020

TAGTTGCGAC CTTTCAAAAC AGTACAGACT ATGTTGAGAC TAAGGTTACA GCTTACAGAA   1080

ACGGAGATTT ACTGCTGGAT CATAGTGGTG CCTATGTTGC CCAATATTAT ATTACTTGGG   1140

ATGAATTATC CTATGATCAT CAAGGTAAGG AAGTCTTGAC TCCTAAGGCT TGGGACAGAA   1200

ATGGGCAGGA TTTGACGGCT CACTTTACCA CTAGTATTCC TTTAAAAGGG AATGTTCGTA   1260

ATCTCTCTGT CAAAATTAGA GAGTGTACCG GGCTTGCCTG GGAATGGTGG CGTACGGTTT   1320

ATGAAAAAAC CGATTTGCCA CTAGTGCGTA AGCGGACGAT TTCTATTTGG GGAACAACTC   1380

TCTATCCTCA GGTAGAGGAT AAGGTAGAAA ATGAC                              1415
```

(2) INFORMATION FOR SEQ ID NO:4:

(i) SEQUENCE CHARACTERISTICS:
        (A) LENGTH: 471 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Asn Lys Ala Val Asn Asp Phe Ile Leu Ala Met Asn Tyr Asp
  1               5                  10                  15

Lys Lys Lys Leu Leu Thr His Gln Gly Glu Ser Ile Glu Asn Arg Phe
             20                  25                  30

Ile Lys Glu Gly Asn Gln Leu Pro Asp Glu Phe Val Val Ile Glu Arg
         35                  40                  45

Lys Lys Arg Ser Leu Ser Thr Asn Thr Ser Asp Ile Ser Val Thr Ala
     50                  55                  60

Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125
```

```
Asp Leu Leu Ala Lys Trp His Gln Asp Tyr Gly Gln Val Asn Asn Val
    130                 135                 140
Pro Ala Arg Met Gln Tyr Glu Lys Ile Thr Ala His Ser Met Glu Gln
145                 150                 155                 160
Leu Lys Val Lys Phe Gly Ser Asp Phe Glu Lys Thr Gly Asn Ser Leu
                165                 170                 175
Asp Ile Asp Phe Asn Ser Val His Ser Gly Glu Lys Gln Ile Gln Ile
                180                 185                 190
Val Asn Phe Lys Gln Ile Tyr Tyr Thr Val Ser Val Asp Ala Val Lys
            195                 200                 205
Asn Pro Gly Asp Val Phe Gln Asp Thr Val Thr Val Glu Asp Leu Lys
        210                 215                 220
Gln Arg Gly Ile Ser Ala Glu Arg Pro Leu Val Tyr Ile Ser Ser Val
225                 230                 235                 240
Ala Tyr Gly Arg Gln Val Tyr Leu Lys Leu Glu Thr Thr Ser Lys Ser
                245                 250                 255
Asp Glu Val Glu Ala Ala Xaa Glu Ala Leu Ile Lys Gly Val Lys Val
                260                 265                 270
Ala Pro Gln Thr Glu Xaa Lys Gln Ile Leu Asp Asn Thr Glu Val Lys
            275                 280                 285
Ala Val Ile Leu Gly Gly Asp Pro Ser Ser Gly Ala Arg Val Val Thr
        290                 295                 300
Gly Lys Val Asp Met Val Glu Asp Leu Ile Gln Glu Gly Ser Arg Phe
305                 310                 315                 320
Thr Ala Asp His Pro Gly Leu Pro Ile Ser Tyr Thr Thr Ser Phe Leu
                325                 330                 335
Arg Asp Asn Val Val Ala Thr Phe Gln Asn Ser Thr Asp Tyr Val Glu
                340                 345                 350
Thr Lys Val Thr Ala Tyr Arg Asn Gly Asp Leu Leu Leu Asp Xaa Ser
            355                 360                 365
Gly Ala Tyr Val Ala Gln Tyr Tyr Ile Thr Xaa Asp Glu Leu Ser Xaa
        370                 375                 380
Xaa His Gln Gly Lys Glu Val Leu Thr Pro Lys Ala Xaa Asp Arg Asn
385                 390                 395                 400
Gly Gln Asp Leu Thr Ala His Phe Thr Thr Ser Ile Pro Leu Lys Gly
                405                 410                 415
Asn Val Arg Asn Leu Ser Val Lys Ile Arg Glu Xaa Thr Gly Leu Ala
                420                 425                 430
Xaa Xaa Xaa Xaa Arg Thr Val Tyr Glu Lys Thr Asp Leu Pro Leu Val
            435                 440                 445
Arg Lys Arg Thr Ile Ser Ile Trp Gly Thr Thr Leu Tyr Pro Gln Val
450                 455                 460
Glu Asp Lys Val Glu Asn Asp
465                 470

(2) INFORMATION FOR SEQ ID NO:5:

(i) SEQUENCE CHARACTERISTICS:
        (A) LENGTH: 471 amino acids
        (B) TYPE: amino acid
        (D) TOPOLOGY: linear (ii) MOLECULE TYPE: protein (xi) SEQUENCE DESCRIPTION: SEQ ID NO:5:

Met Ala Asn Lys Ala Val Asn Asp Phe Ile Leu Ala Met Asn Tyr Asp
```

-continued

```
  1                   5                  10                  15

Lys Lys Lys Leu Leu Thr His Gln Gly Glu Ser Ile Glu Asn Arg Phe
             20                  25                  30

Ile Lys Glu Gly Asn Gln Leu Pro Asp Glu Phe Val Val Ile Glu Arg
             35                  40                  45

Lys Lys Arg Ser Leu Ser Thr Asn Thr Ser Asp Ile Ser Val Thr Ala
        50                  55                  60

Thr Asn Asp Ser Arg Leu Tyr Pro Gly Ala Leu Val Val Asp Glu
 65                  70                  75                   80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
            130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp Xaa Ser
            355                 360                 365

Gly Ala Tyr Val Ala Gln Tyr Tyr Ile Thr Xaa Asp Glu Leu Ser Xaa
            370                 375                 380

Xaa His Gln Gly Lys Glu Val Leu Thr Pro Lys Ala Xaa Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Xaa Thr Gly Leu Ala
            420                 425                 430
```

```
Xaa Xaa Xaa Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470
```

(2) INFORMATION FOR SEQ ID NO:6:

(i) SEQUENCE CHARACTERISTICS:
        (A) LENGTH: 471 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Xaa Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Xaa Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Xaa Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala Xaa Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300
```

-continued

```
Gly Lys Val Asp Met Val Glu Asp Leu Ile Gln Glu Gly Ser Arg Phe
305             310                 315                 320

Thr Ala Asp His Pro Gly Leu Pro Ile Ser Tyr Thr Thr Ser Phe Leu
            325                 330              335

Arg Asp Asn Val Val Ala Thr Phe Gln Asn Ser Thr Asp Tyr Val Glu
            340             345              350

Thr Lys Val Thr Ala Tyr Arg Asn Gly Asp Leu Leu Leu Asp Xaa Ser
        355             360              365

Gly Ala Tyr Val Ala Gln Tyr Tyr Ile Thr Xaa Asp Glu Leu Ser Xaa
        370             375          380

Xaa Xaa Gln Gly Lys Xaa Val Leu Thr Pro Lys Ala Xaa Asp Arg Asn
385             390              395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Xaa Thr Gly Leu Xaa
            420             425              430

Xaa Xaa Xaa Xaa Arg Thr Val Tyr Glu Lys Thr Asp Leu Pro Leu Val
        435             440              445

Arg Lys Arg Thr Ile Ser Ile Trp Gly Thr Thr Leu Tyr Xaa Gln Val
    450             455              460

Glu Asp Lys Val Glu Asn Asp
465             470
```